United States Patent [19]
Ferre et al.

[11] Patent Number: 5,803,089
[45] Date of Patent: Sep. 8, 1998

[54] POSITION TRACKING AND IMAGING SYSTEM FOR USE IN MEDICAL APPLICATIONS

[75] Inventors: Maurice R. Ferre, North Andover; Peter D. Jakab, Canton; James S. Tieman, Watertown, all of Mass.

[73] Assignee: Visualization Technology, Inc., Woburn, Mass.

[21] Appl. No.: 527,517

[22] Filed: Sep. 13, 1995

Related U.S. Application Data

[63] Continuation-in-part of Ser. No. 306,818, Sep. 15, 1994.

[51] Int. Cl.⁶ ............................... A61B 19/00
[52] U.S. Cl. .................................... 128/897
[58] Field of Search ................... 128/897–898; 606/1

[56] References Cited

U.S. PATENT DOCUMENTS

| | | |
|---|---|---|
| 4,256,112 | 3/1981 | Kopf et al. . |
| 5,207,688 | 5/1993 | Carol . |

FOREIGN PATENT DOCUMENTS

2 164856   4/1986   United Kingdom .

*Primary Examiner*—John P. Lacyk
*Attorney, Agent, or Firm*—Samuels, Gauthier, Stevens & Reppert

[57] ABSTRACT

A system is disclosed for monitoring the position of a medical instrument with respect to a patient's body and for displaying at least one of a plurality of prerecorded images of said body responsive to the position of said medical instrument. In one embodiment the system includes a reference unit secured from movement with respect to the patient's body such that said reference unit is substantially immobile with respect to a target operation site. The system also includes a remote unit for attachment to the medical instrument. A field generator may be associated with one of the units for generating a position characteristic field in an area including the target operation site. One or more field sensors may be associated with either of the units responsive to the presence of the position characteristic field for producing one or more sensor output signals representative of said sensed field. A position detector in communication with the sensor output signal produces position data representative of the position of the remote unit with respect to the reference unit. An output display in communication with the position detector displays at least one of the prerecorded images responsive to the position data.

10 Claims, 12 Drawing Sheets

POSITION TRACKING AND IMAGING SYSTEM FOR USE IN MEDICAL APPLICATIONS

This is a continuation-in-part of copending application Ser. No. 08/306,818 filed on Sep. 15, 1994.

BACKGROUND OF THE INVENTION

The invention relates to computer assisted medical surgery and in particular relates to systems for displaying prerecorded visual images during surgical operations.

Presently available medical imaging techniques such as CAT (Computerized Axial Tomography), MRI (Magnetic Resonance Imaging), and PET (Position Emission Tomography), are known to be helpful not only for diagnostic purposes, but also for providing assistance during surgery. Prerecorded images may be displayed during surgical operations to provide the surgeon with illustrative reference mappings of pertinent portions of a patient's body.

Tracking systems for monitoring the position of a medical instrument have also been developed for use with image display systems. Generally, as the surgeon moves the medical instrument with respect to the patient's body, associated prerecorded images are displayed responsive to the movement of the instrument. Such tracking systems typically involve either the use of a passive articulated arm attached to the medical instrument, optical detection or ultrasonic detection.

Tracking systems using a passive articulated mechanical arm attached to a medical instrument are disclosed in U.S. Pat. Nos. 5,186,174 and 5,230,623. Generally, as the surgeon moves the surgical instrument with respect to the patient's body, micro recorders at the joints of the articulated arm record the respective amounts of movement of each arm member. The outputs of the micro recorders are processed and the position of the medical instrument with respect to the base of the articulated arm is thereby monitored. One or more prerecorded images are then displayed responsive to the movement of the surgical instrument. Such articulated arm tracking systems, however, require that the instrument be attached to a cumbersome mechanical arm. Also, although free movement of the tip of the arm in three dimensional space may be theoretically possible, the surgeon might experience difficulty positioning the instrument at certain locations and in desired orientations within the body.

Tracking systems using optical detection (video cameras and/or CCDs (Charge Coupled Devices)) have been proposed for monitoring the position of a medical instrument with respect to a reference unit as mentioned in U.S. Pat. No. 5,230,623. Such systems, however, require that the reference unit and the instrument both be within the view of the camera. This not only limits the movement of the surgical staff, but also requires that at least a portion of the medical instrument remain outside the patient's body.

Tracking systems using ultrasonic detection are generally disclosed in U.S. Pat. No. 5,230,623. Such systems, however, are disclosed to be used in a fashion similar to optical detection, i.e., triangulation of transmitted signals. The transmitted signals are sent from one or more senders to associated receiver(s), and the distances travelled by the signals are determined from either timing or amplitude changes. Again, the transmission path must remain unobstructed.

A further shortcoming common to each of the above tracking systems is that the patient must not move during the operation. Although the patient is likely to be generally anesthetized, the patient's body may be inadvertently moved by the surgical staff, or the surgeon may want to move the body for better positioning. If the body is moved after the tracking system has been initialized, then the tracking will be misaligned.

There is a need therefore for a system for monitoring the position of a medical instrument with respect to a patient's body that avoids these and other shortcomings of present devices.

SUMMARY OF THE INVENTION

The invention relates to a system for monitoring the position of a medical instrument with respect to a patient's body and for displaying at least one of a plurality of prerecorded images of the body responsive to the position of the medical instrument. The system includes a reference unit, a remote unit, a position characteristic field generator, a field sensor, a position detection unit and an output display.

In one embodiment, the reference unit is secured from movement with respect to at least a portion of the patient's body such that the reference unit is substantially immobile with respect to a target operation site. The remote unit is attached to the medical instrument. The field generator is associated with one of the reference or remote units and generates a position characteristic field, such as a multiplexed magnetic field, in an area including the target operation site. The field sensor is associated with the other of the reference or remote units and is responsive to the presence of the field for producing a sensor output signal representative of the sensed field.

The position detection unit is in communication with the sensor output signal and produces position data representative of the position of the remote unit with respect to the reference unit. The output display unit is in communication with the position detection unit for displaying at least one of the prerecorded images responsive to the position data.

The system further may include a registration unit in communication with a storage unit and the position data. The storage unit stores the plurality of prerecorded images of the body. Each prerecorded image is representative of a planar region within the body such that the plurality of planar regions represented by the prerecorded images define a first coordinate system. The registration unit correlates the position data of a second coordinate system (as defined by the position detection unit) with the plurality of prerecorded images of the first coordinate system, and identifies a desired prerecorded image associated with the position of the remote unit with respect to the patient's body.

The invention also relates to a reference unit that is attachable to a patient's head, and a medical instrument, such as an aspirating device, that is adapted to removably receive a position detection unit.

BRIEF DESCRIPTION OF THE DRAWINGS

The following detailed description of the invention may be further understood with reference to the accompanying drawings in which.

DETAILED DESCRIPTION OF THE ILLUSTRATED EMBODIMENTS

Figure 1:
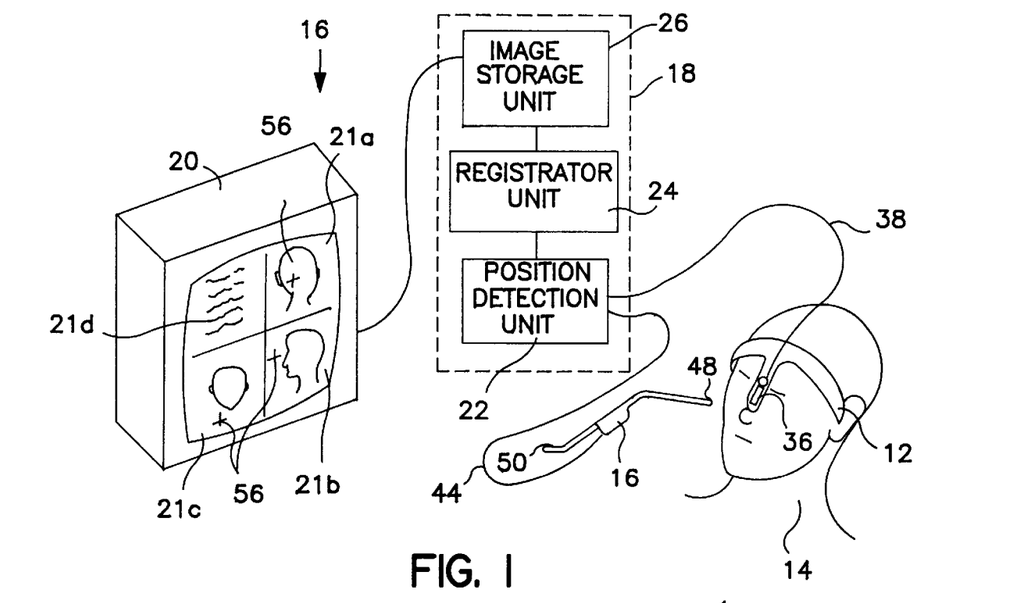
FIG. 1 is a diagrammatic view of a system of an embodiment of the invention.

As shown in FIG. 1, a system 10 of the invention includes a headset 12 mounted on a patient 14, a medical instrument 16, a control system 18 and a display 20. The control system 18 includes a position detection unit 22, a registration unit 24, and an image storage unit 26.

The image storage unit 26 stores sets of prerecorded images such as CAT, MRI or PET scan images. Each set of images may be taken along, for example, coronal, sagittal or axial directions. AS shown in FIG. 1, the display 20 shows three images, a coronal image 21a, a sagittal image 21b, and an axial image 21c. Text information may also be displayed as shown at 21d in FIG. 1.

Figure 2:
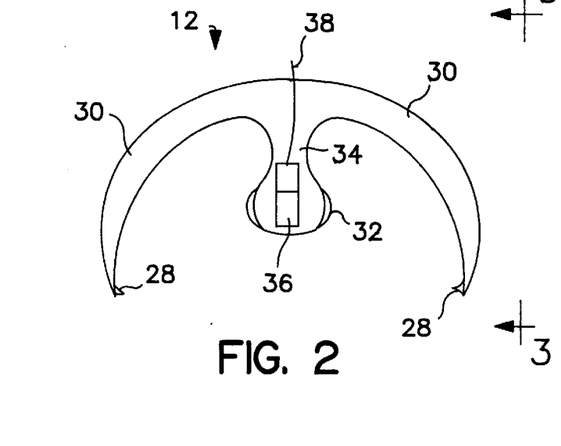
FIG. 2 is a front view of the headset unit shown in FIG. 1.
Figure 3:
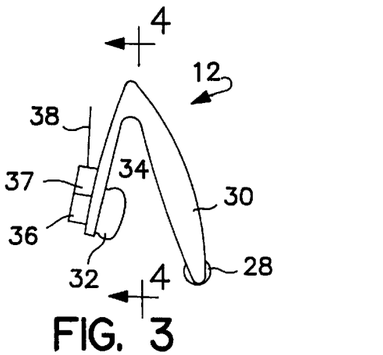
FIG. 3 is a side view of the headset unit shown in FIG. 1 taken along line 3—3 of FIG. 2.
Figure 4:
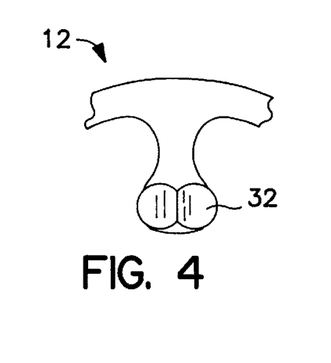
FIG. 4 is a rear view of a portion of the headset shown in FIG. 1 taken along line 4—4 of FIG. 3.

As further shown in FIGS. 2–4, the headset 12 includes two ear mounts 28 on side members 30, and a nose bridge mount 32 on a center member 34. The headset 12 should be made of a resilient plastic such that it may be snugly attached to a patient's head, and may be provided in a variety of sizes. A primary objective of the headset is to provide a reference unit that may be easily attached to and removed from a patient's head wherein the headset may be repeatedly reattached in exactly the same place with a high degree of accuracy. In other embodiments, the side members 30 of the headset 12 may be rotationally attached to one another and the ear mounts 28 may be biased toward one another. Further, the center member 34 may be rotatable with respect to the side members 30 and biased toward the ear mounts 28 as well.

The headset 12 shown in FIGS. 1–4 also includes a reference unit 36 connected to the position detection unit 22 via communication lines 38. The reference unit 36 may be releasably attached to the headset 12 by conventional clamp or fastening means. In one embodiment the reference unit 36 may include a position characteristic field generator capable of generating a multidirectional field in three dimensions and may involve the use of either electromagnetic or ultrasonic waves. The position characteristic field differs from the transmit/receive triangulation system, in part, because it does not rely on the comparison of one transmitted signal with another as does triangulation. This permits the path between the field generator and the remote sensor to be obstructed by materials that do not significantly alter the generated field. For example, the position of the medical instrument could be identified even when the instrument is within the patient's body when the generated field is a magnetic field. Additionally, the reference unit may also include a reference sensor 37 to provide verification of proper system operation.

In the present embodiment the field generator includes three orthogonally disposed magnetic dipoles (e.g., current loops or electromagnets), and the orthogonally disposed magnetic fields generated by each of the three dipoles are mutually distinguishable from one another (e.g., via either phase, frequency, or time division multiplexing). The near-field characteristics of the multiplexed magnetic fields may be relied upon for position detection, for example as generally described in U.S. Pat. No. 4,054,881. In alternate embodiments the field generator may be located somewhere other than on the headset and the headset may include two field sensors 36,37. When the distance between the sensors 36,37 is known, the second sensor may be used to act as a backup or reference check for monitoring the proper operation of the system. If the sensed fields are inconsistent then an error signal is displayed and/or sounded.

In other embodiments the headset 12 may be employed in systems based on the triangulation of signals where the reference unit 36 includes one or more signal transmitters and/or one or more signal receivers. In such a triangulation system, position detection is achieved by comparing certain characteristics of one transmitted signal with those of a second transmitted signal to determine the relative distances travelled. The transmitted signals may be electromagnetic (e.g., radio, laser light or light emitting diodes) or may be ultrasonic. The position of the patient's head with respect to the surgical instrument may thereby be monitored.

Figure 5:
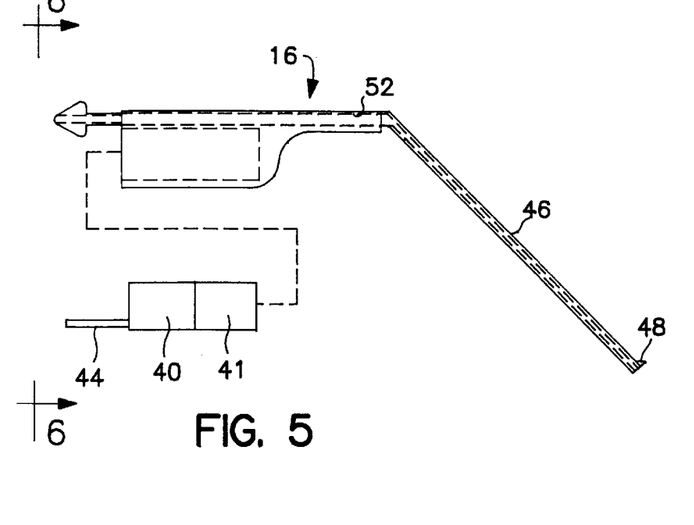
FIG. 5 is an exploded side view of the surgical instrument and remote sensor shown in FIG. 1.
Figure 6:
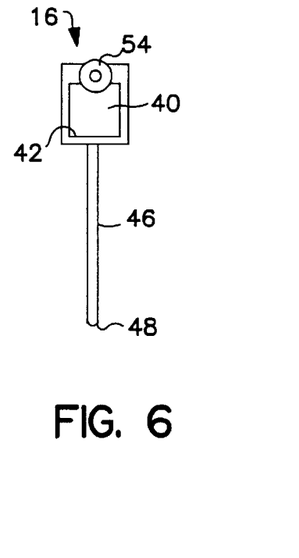
FIG. 6 is an end view of the assembled surgical instrument and sensor shown in FIG. 1 taken along line 6—6 of FIG. 5.

As shown in FIGS. 5 and 6 the medical instrument 16 may be an aspirating device adapted to removably receive a remote sensor 40 for detecting, for example, the field generated by the position characteristic field generator. The sensor 40 may be held inside the instrument 16 by force fit sizing or through the use of a resilient snap member in the wall opening 42. Since an aspirating device is commonly used in most surgical operations, incorporating the remote sensor into the aspirating device provides the surgeon with a convenient position detection device that does not clutter the operation site with unnecessary items. The instrument 16 may further include a second backup field sensor 41 for system error detection as discussed above with reference to the sensor 37.

The remote sensors 40,41 are removable from the aspirating device and may be interchangeably inserted into any of a variety of specially adapted surgical instruments. In the illustrated embodiment, the remote sensors 40,41 are received through an opening 42 in the proximal end of the instrument 16, and are connected to the position detection unit 22 via communication lines 44. The sensors 40,41 may also each include three orthogonally disposed dipole sensing elements for detecting the presence of the field generated by the field generator. For example, in one embodiment, the field generator and the sensors each include three orthogonally disposed electrical wire loops. The generator produces an alternating current through one generator loop at a time thus generating a time division multiplexed alternating electromagnetic field. The sensor loop signals are each processed in synchronous timing with the generator loops to produce outputs responsive to each respective alternating electromagnetic field.

The distal end of the instrument 16 includes a rigid aspirating tube 46 having a flared tip 48. The position of the tip 48 with respect to the center of the remote sensor 40 is a known constant and may be easily seen by the surgeon during surgery. The aspirating tube 46 is in fluid communication with an aspirating catheter 50 through the proximal end of the instrument 16 via internal channel 52 and a connector element 54. The aspirating catheter 50 (shown in FIG. 1) is connected to a vacuum aspirating unit (not shown).

In operation, the position detection unit monitors the position of the medical instrument 16 with respect to the reference unit 36. The registration unit 24 correlates the changes in position of the instrument 16 with the spacial orientation of the stored images. As the surgeon moves the medical instrument 16, images appear on the display 20 responsive to the position of the medical instrument 16. This permits the surgeon to always have available the coronal, sagittal, and axial views associated with the precise location of the tip 48 of the instrument 16 regardless of whether the tip 48 is inside of the patient 14. Moreover, since the field generator is attached to the patient's head, the patient is free to be moved without loss of the tracking capabilities. The display 20 may further identify the location of the tip 48 on each of the displayed images as shown at 56 in FIG. 1. In other embodiments the orientation of the aspirating tube 46 may also be identified on the displayed images. In further embodiments, a three dimensional composite image may be displayed based on the prerecorded images.

Figure 7:
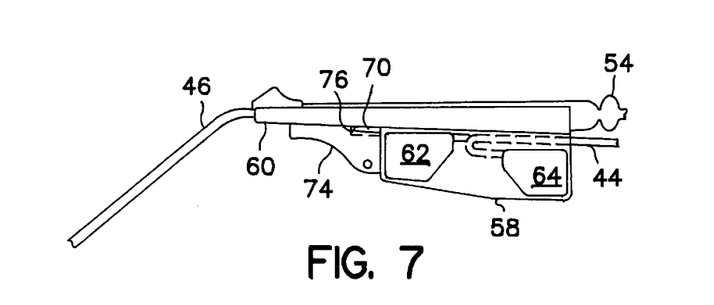
FIG. 7 is a side view of another embodiment of a surgical instrument and sensor unit of the invention in accordance with an alternative embodiment of the invention.
Figure 8:
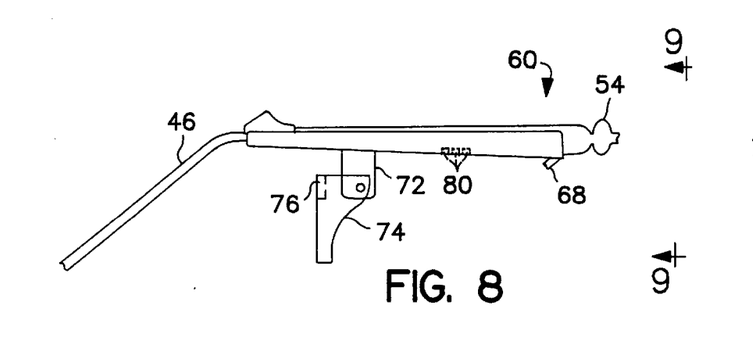
FIG. 8 is a side view of the surgical instrument shown in FIG. 7.
Figure 9:
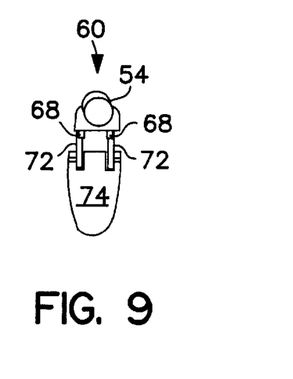
FIG. 9 is an end view of the surgical instrument shown in FIG. 7.
Figure 10:
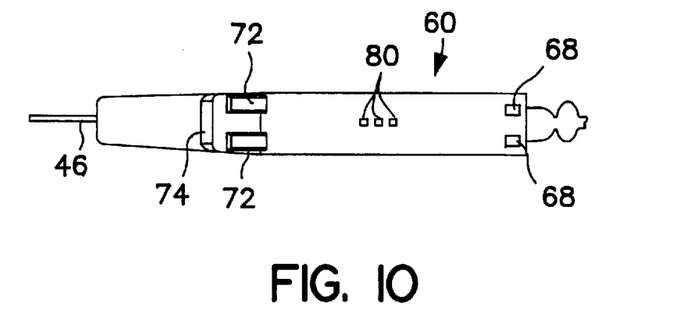
FIG. 10 is an elevational view of the surgical instrument shown in FIG. 7.

As shown in FIGS. 7–11 another embodiment of a removable remote sensor unit 58 may be used with an aspirating device 60. The sensor unit 58, including two sensors 62,64 may be removably attached to the device 60 by first engaging recesses 66 on the unit 58 with fingers 68 on the device 60. A tounge 70 on the unit 58 is then received between hinge posts 72 on the device 60, and finally secured in place by rotating the lock 74 from an open position as shown in FIG. 8 to a closed position as shown in FIG. 7. The lock 74 includes a recessed area at 76 adapted to frictionally engage the tounge 70 on the sensor unit 58.

Figure 11:
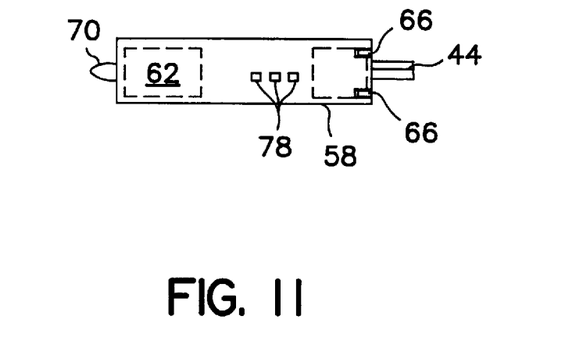
FIG. 11 is a plan view of a remote sensor unit that is adapted to be used with the surgical instrument shown in FIGS. 7–10.

The sensor unit 58 further includes the ability to identify which of a plurality of medical instruments is attached to the sensor unit 58 at any time. Specifically, the unit 58 includes a plurality of Hall effect transistors 78, and the medical instrument 60 includes one or more tiny permanent magnets 80. By the number and/or positioning of the magnets 80, the transistors 78 identify which of the medical instruments is attached to the sensor unit 58.

Figure 12:
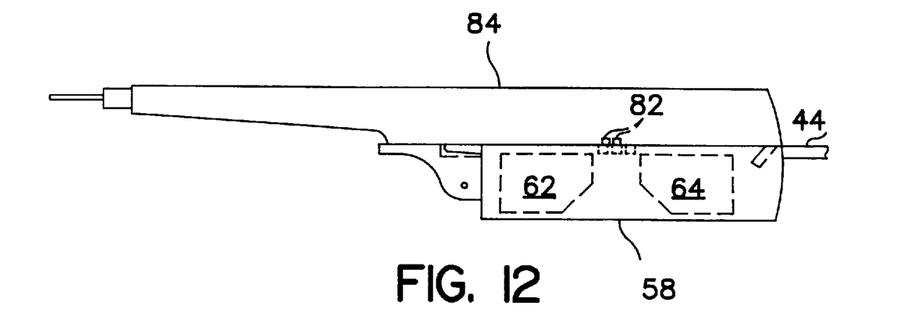
FIG. 12 is a side view of another surgical instrument together with the removable remote sensor unit shown in FIGS. 7 and 11.
Figure 13:
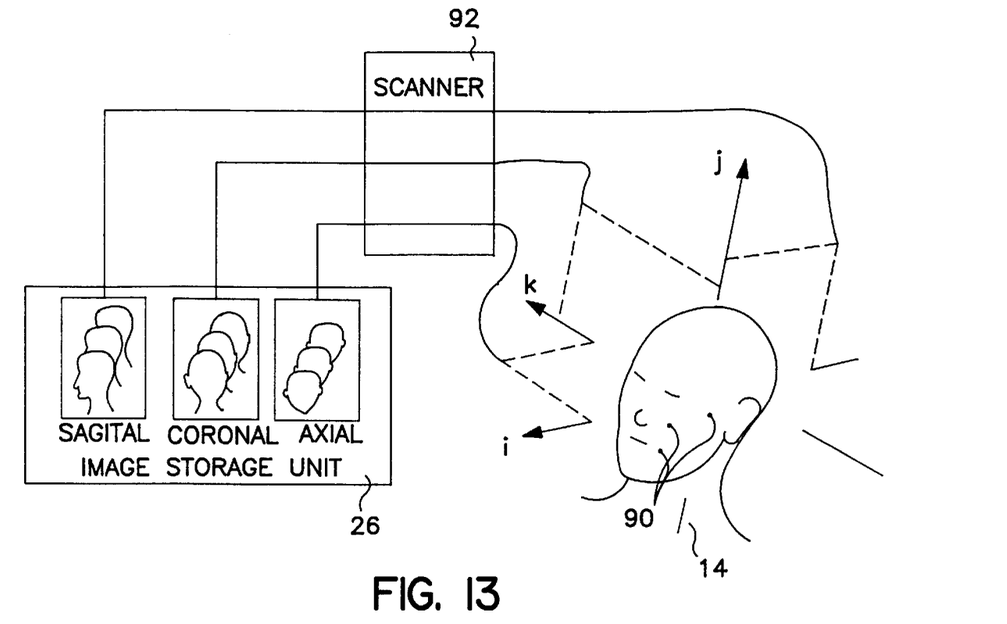
FIG. 13 is a diagrammatic illustration of the system employed to prerecord CT images for use with the system of the invention.
Figure 14:
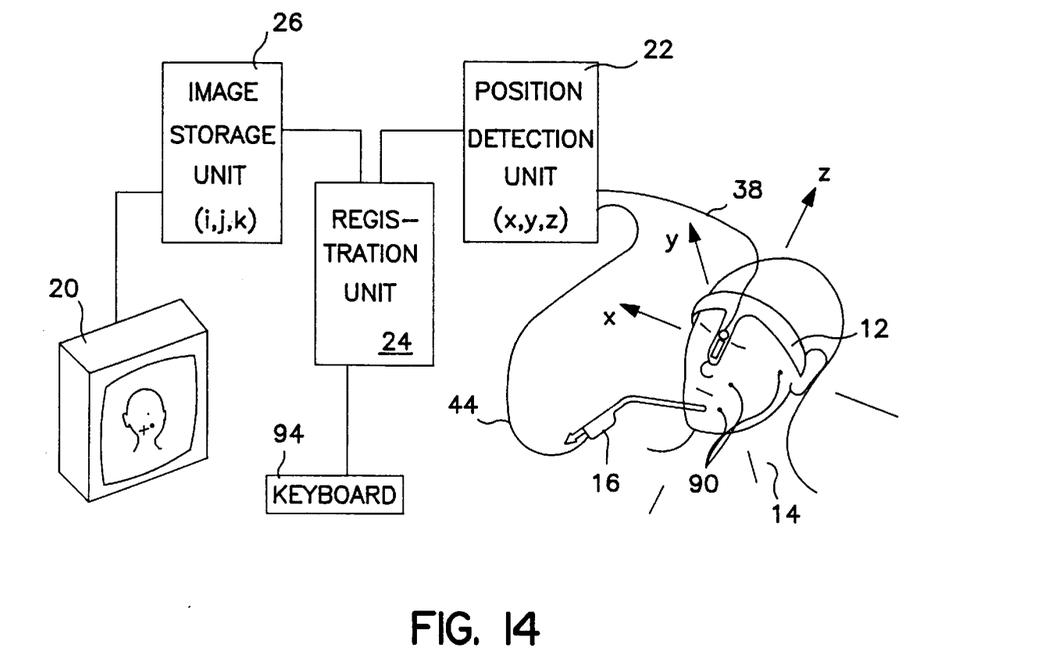
FIG. 14 is diagrammatic illustration of a manual registration process of the invention.

For example, if all of the transistors 78 sense the presence of a magnet 80 then the instrument 60 shown in FIGS. 7–11 is known to be attached to the sensor unit 58 since the instrument 60 includes three magnets. If only two magnets 82 are sensed then the medical instrument attached to the sensor unit 58 is a different instrument 84 as shown in FIG. 12. If no magnets are sensed then it is known that the sensor unit 58 is not attached to any medical instrument. Knowing the identity of the attached medical instrument permits the system to automatically adjust the position detection unit to compensate for the differences in instrument tip position with respect to the position of the sensors 62,64 for a variety of medical instruments. The removably engageable feature of the sensor unit not only provides versatility, but also facilitates the use of sterilized medical instruments. As illustrated in FIGS. 13 and 14 the registration process involves two fundamental steps: 1) recording the scan images of a predetermined orientation and 2) mapping the spacial orientation of the position detection system onto the recorded images. For example, the orientations of the prerecorded images may be in the sagittal (i-j plane), coronal (k-j plane) and/or axial (k-i plane) as shown in FIG. 13. The images may be digitally stored and the distance between each scanned image is recorded, as are the relative orientations of each set of images. As those skilled in the art will appreciate, in alternative embodiments certain of the images may be created from other images without the need to prerecord each of the sagittal, coronal and axial views. For example, by multiplanar reformatting the sagittal and coronal images may be created from the axial images.

In one embodiment, fiducial markers 90 are placed on the patient's head 14 prior to scanning with the scanner 92. The markers then appear on certain of the scanned images, and may be located by the position detection system as shown in FIG. 14. Specifically, when each marker 90 is sequentially located, for example with the tip 48 of a medical instrument 16, the user locates the same marker on the prerecorded images by using, for example a computer mouse. The user then controls the entering of the registration data through either a computer keyboard 94, a mouse, or a foot switch. In alternative embodiments the registration unit may scan each prerecorded digital image beginning from one corner until it locates the identified marker.

Figure 15:
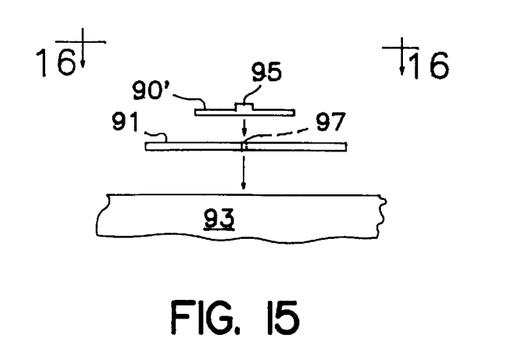
FIG. 15 is an elevational view of the components of a fiducial marker system in accordance with an embodiment of the invention.
Figure 16:
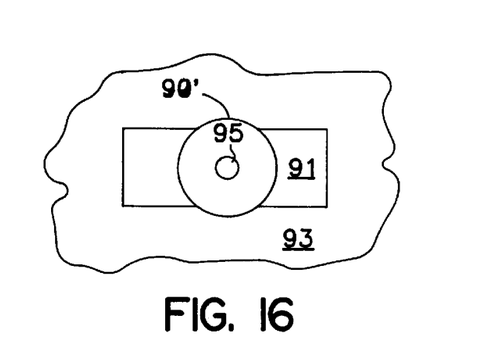
FIG. 16 is a plan view of the components of the system of FIG. 15 taken along line 16—16 thereof.

In further embodiments involving the use of fiducial markers that are placed on the patient's body (e.g., face) prior to recording the scan images, fiducial markers 90' may be adhered to intermediate adhesive strips 91 which are directly adhered to the patient's skin 93 as shown in FIGS. 15 and 16.

Figure 17:
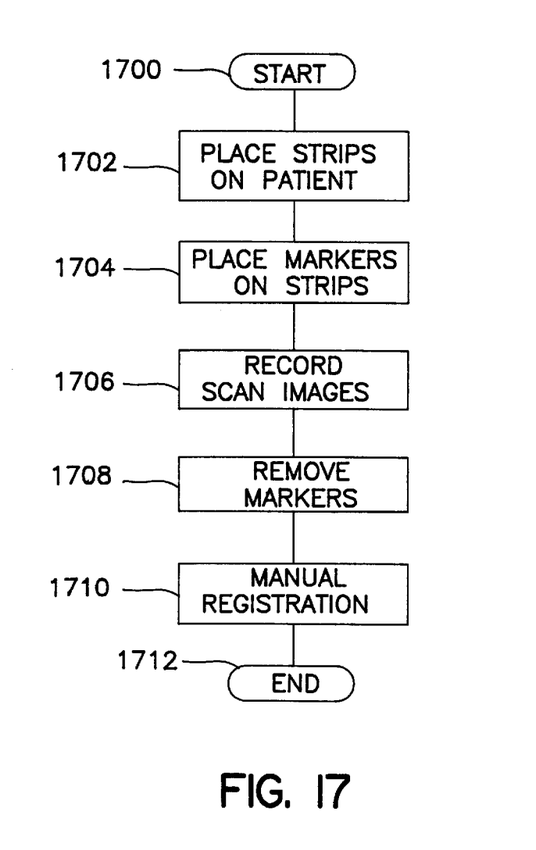
FIG. 17 is a flowchart of the process of using the fiducial marker system of FIG. 15.

The fiducial markers 90' include a radiopaque element 95 and the strips 91 include a small puncture hole or other marker 97. With reference to FIG. 17, the process of using the fiducial markers 90' begins (step 1700) by first placing the strips 91 on the patient's skin (step 1710). The fiducial markers 90' are then placed on the strips 91 such that the radiopaque elements 95 align with the markers 97 on the strips 91 (step 1704). The scan images are then recorded (step 1706), and the fiducial markers 90' may then be removed from the patient (step 1708). During manual registration the surgeon or technician may locate the markers 97 with the tip of a pointer (step 1710) and thereby record the positions of the fiducial marker radiopaque elements 95 with respect to the transmitter. The use of the intermediate strips 91 not only provides increased comfort to the patient after the image scanning and prior to surgery, but also facilitates accurate registration. Since the radiopaque elements 95 were centered directly on top of the markers 93, the accuracy of registration is enhanced because the user may now locate the smaller sized markers 93 instead of more indefinitely locating a portion of the larger sized radiopaque elements 95 with the pointer tip.

Once each of the markers has been located using the position detection unit, the registration unit generates a mapping function to translate the position detection data (in x-y-z coordinates) to the stored image orientation data (in i-j-k coordinates). In particular, the mapping equation is determined by using Powell's method as follows.

The images points are each processed as a matrix of the form $$\begin{bmatrix} i_I \\ j_I \\ k_I \end{bmatrix} \quad (1)$$

and the collected sensor points are each processed as a matrix of the form $$\begin{bmatrix} x_s \\ y_s \\ z_s \end{bmatrix} \quad (2)$$

A computer processor then iteratively calculates the optimal values for the transformation matrices $$\begin{bmatrix} r_{11} & r_{12} & r_{13} \\ r_{21} & r_{22} & r_{23} \\ r_{31} & r_{32} & r_{33} \end{bmatrix} \text{ and } \begin{bmatrix} t_x \\ t_y \\ t_z \end{bmatrix} \quad (3)$$

to solve the following equation:

$$\begin{bmatrix} i_I \\ j_I \\ k_I \end{bmatrix} = \begin{bmatrix} r_{11} & r_{12} & r_{13} \\ r_{21} & r_{22} & r_{23} \\ r_{31} & r_{32} & r_{33} \end{bmatrix} \cdot \begin{bmatrix} x_s \\ y_s \\ z_s \end{bmatrix} + \begin{bmatrix} t_x \\ t_y \\ t_z \end{bmatrix} \quad (4)$$

such that $(i_c-i_i)^2+(j_c-j_i)^2+(k_c-k_i)^2$ is a minimum for the summation of all of the collected image points. The optimization method employs distance minimization, and at least three image points are required for this method.

The optimal values for the transformation matrices comprise the transformation equation and may now be used to translate the position of the medical instrument with respect to the transmitter in the x-y-z coordinate system, to the appropriate orientation of the prerecorded images in the i-j-k coordinate system.

A further embodiment of the headset of the invention may be employed in an automatic registration process. For example, as shown in FIGS. 18 and 19 another embodiment of a headset 100 of the invention includes two ear mounts 28, side members 30, and a nose bridge mount 32 on center member 34 as discussed above with reference to FIGS. 2–4.

Figure 21:
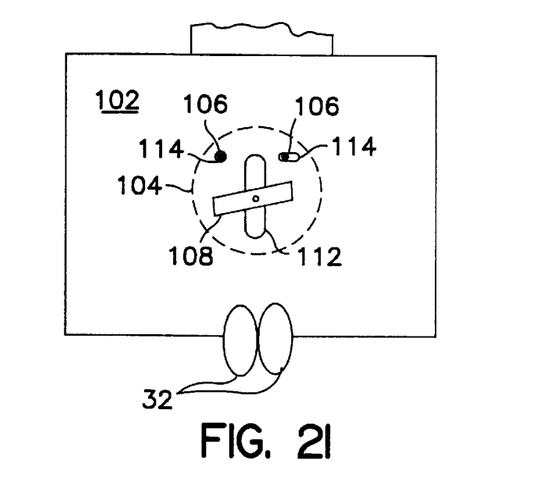
FIG. 21 is a partial view of a portion of the headset shown in FIG. 16 taken along line 21—21 thereof.

The headset 100 further includes a center plate 102 on the center member 34. The center plate 102 is adapted to receive a transmitter 104 as shown in phantom in FIG. 19 and shown from the underside of the plate 102 in FIG. 21. The transmitter 104 includes two posts 106 and a key 108 that is free to rotate about a pin 110.

Figure 20:
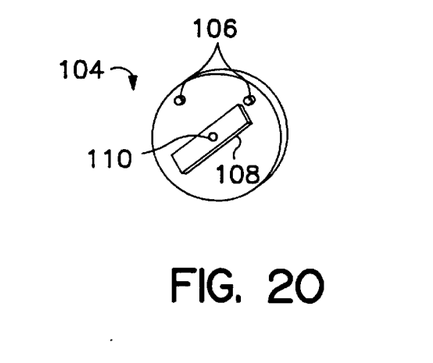
FIG. 20 is a plan view of a transmitter that is adapted to be used with the headset unit shown in FIG. 18.

To install the transmitter 104 on the center plate 102, the key is passed through a longitudinal opening 112 in the plate 102, and the posts 106 are each received by post openings 114. One of the post openings 114 is preferably formed as a slot to provide a snug fit for the transmitter yet still accommodate variations between headsets due to manufacturing tolerances. The key 108 may then be rotated to lock the transmitter onto the outer facing surface of the plate 102. The transmitter 104 may then be removed from and reattached to identical headsets in the same location and orientation with a high degree of accuracy.

Figure 18:
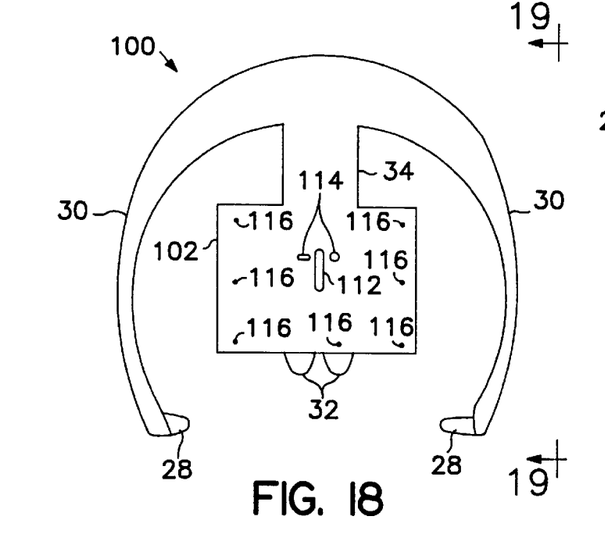
FIG. 18 is a side view of a headset unit in accordance with another embodiment of the invention.
Figure 19:
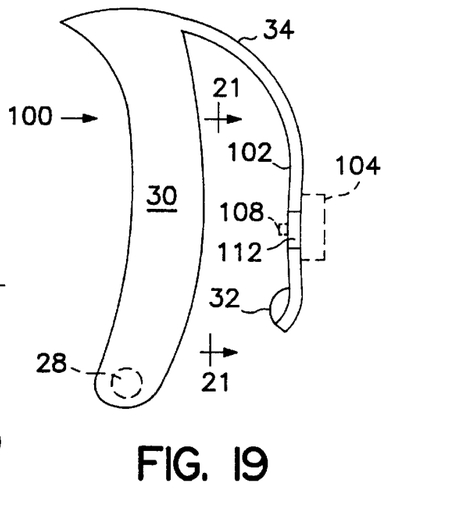
FIG. 19 is an end view of the headset unit shown in FIG. 18 taken along line 19—19 thereof.

The headset 100 further includes very small (e.g., about 2 mm dia.) metal fiducial balls 116 secured within the center plate 102 as shown in FIG. 18. The automatic registration process locates the balls 116 on the prerecorded scan images, and knowing the spacial relationship between the balls 116 and the transmitter 104, automatically generates the mapping function to translate from the transmitter coordinate system to the image coordinate system.

Figure 22:
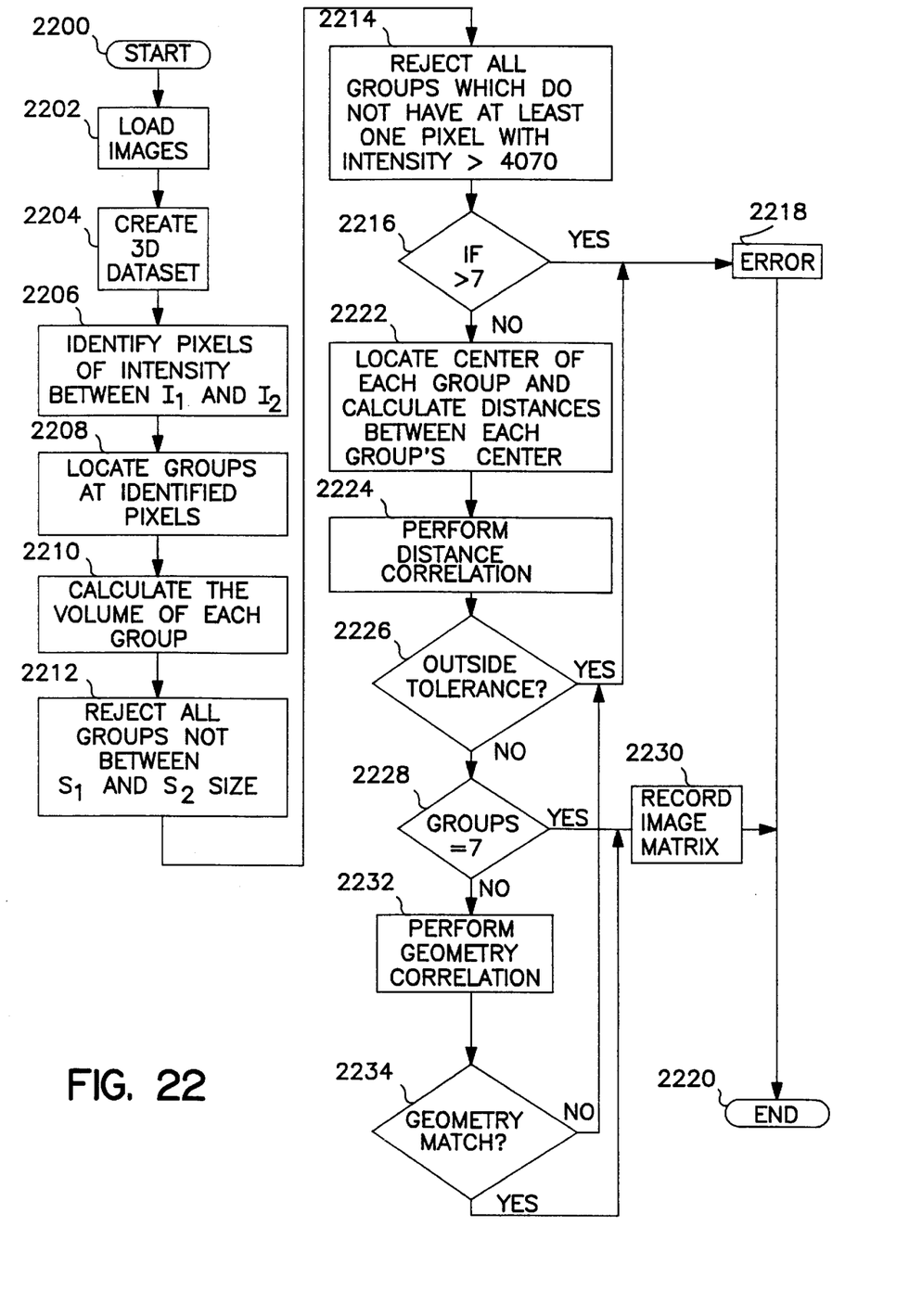
FIG. 22 is a flow chart of an automatic registration process of the invention.

Specifically and with reference to FIG. 22, the automatic registration process begins (step 2200) by loading the prerecorded images (step 2202) and then creating a three dimensional data set (step 2204). Pixels having an intensity within a certain range are then identified (step 2206), and groups of adjacent pixels are located (step 2208) and classified together as a single group. The volume of each group is calculated (step 2210) and groups not within a predefined range of volumes are rejected (step 2212). Groups not having at least one pixel with an intensity level of at least a certain amount are rejected (step 2214). If the number of groups remaining is less than the number of fiducial balls 116 (step 2216), e.g., 7, then the program ends having failed to provide automatic registration (steps 2218 and 2220).

The center of each group is then located and the distances between each group's center and the other centers are calculated and recorded in a matrix of at least 7 by 7 (step 2222). The known distances between the fiducial balls comprise a predefined 7 by 7 matrix. The program then compares each of the known distances with the various predefined distances between the fiducial balls, then generates a best fit approximation of the correlation between the sets of distances (step 2224). If the distance correlation provides an approximation outside of a preset tolerance (step 2226) then the program ends (steps 2218 and 2220) having failed to automatically generate the transformation matrices. If the correlation of distances is within tolerance and there are seven groups (step 2228) then the image data is recorded in the image matrix (step 2230). If the number of groups is above seven, then a geometry correlation is performed comparing the geometry of the groups to the known geometry of the fiducial balls (step 2232). If the geometry correlation is successful (step 2234) then the transformation matrices are recorded (step 2230), and if not the program reports the error condition (step 2218).

Having successfully generated the image point matrix (step 2230), and since the sensor point matrix is based on the known layout of the fiducial markers with respect to the transmitter, the mapping equation may now be automatically generated as discussed above with reference to Powell's method.

In other embodiments wherein the patient is wearing a reference unit when the scan images are prerecorded the registration program may automatically locate portions of the reference unit itself on the scanned images, thereby identifying the orientation of the reference unit with respect to the scanned images. Again, since the relative orientation of the field generator with respect to the reference unit is known, the registration unit may then generate the appropriate mapping function. In further embodiments the surfaces of the patient's skin may be tracked such as by a laser light pointer or a movable tip pointer that is biased in a forward direction. The tracked surfaces may then be located on the stored images. In still further embodiments, the registration unit could be programmed to identify characteristic structures or features of the patient's body and thereby provide fully automatic registration. For example, the system might, knowing the size and shape of a headset, identify where the headset would be placed on the patient's head, even though it does not appear on the prerecorded images.

The position detection system may operate by any desired principle suitable for generating a field in which position detection may be achieved at any location within the field. For example, it has been found that the 3 Space® Fastrak™ product sold by Polhemus, Incorporated of Colchester, Vt. operates via principles suitable for use in the present invention. This product uses three orthogonally disposed magnetic dipoles for both the transmitter and the sensor, and produces alternating electromagnetic fields of 8–14 kHz that are time division multiplexed.

Figure 23:
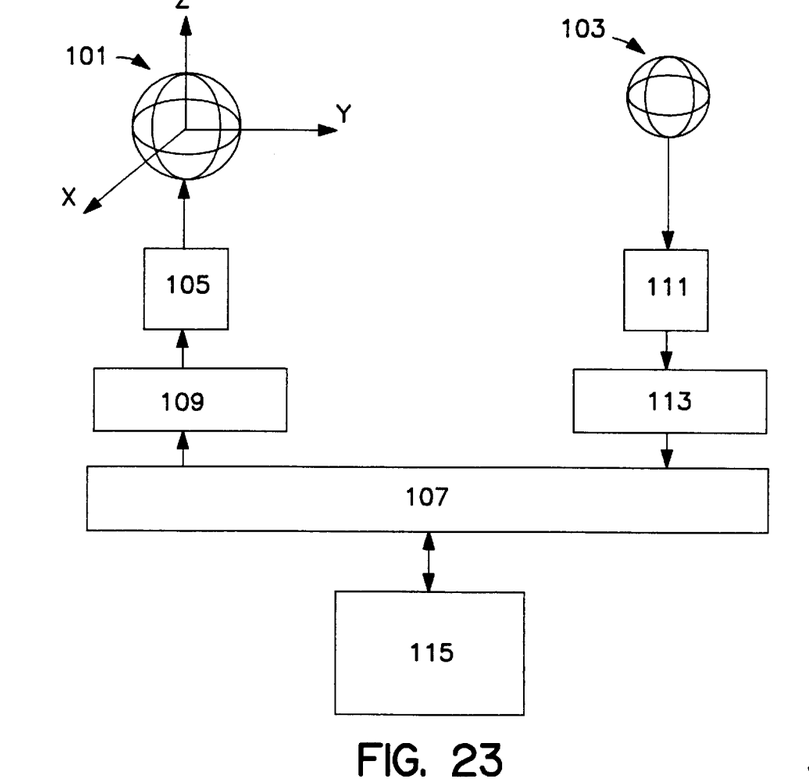
FIG. 23 is a diagrammatic view of the position detection components in accordance with a system of the invention.

Specifically and with reference to FIG. 23, both the magnetic field source 101 and the magnetic field sensor 103 include three orthogonally disposed coils as shown. An alternating electric current from an amplifier 105 is passed through each of the source coils one at a time generating sequential magnetic fields. A processing unit 107 generates the timing signals and controls a digital-to-analog converter 109. The magnetic fields induce voltages in the three coils of the sensor 103. The induced voltages are amplified by an amplifier 111, digitized by an analog-to-digital converter 113, and then processed by the processing unit 107.

The time division multiplexed excitation of the three coils of the source creates a unique magnetic field sequence throughout the field of the source. For every location in the field of the source, the six degree of freedom data can be calculated from the data present on the three coils of the sensor. The six degree of freedom information is then sent to a host computer 115.

The position of a sensor S with respect to the field generator defining a reference coordinate frame (X,Y,Z) may be produced by the 3 Space® Fastrak™ product at a given time as a set of six values $x_s$, $y_s$, $z_s$, $\omega_{azs}$, $\omega_{els}$, and $\omega_{ros}$. The values $x_s$, $y_s$, and $z_s$ identify the position of the center of the sensor within the X,Y,Z coordinate reference frame, and the angles $\omega_{azs}$, $\omega_{els}$, and $\omega_{ros}$ identify the orientation of the sensor S with respect to the X,Y,Z coordinate reference frame.

The value $\omega_{azs}$ is the azimuth angle of the sensor. The azimuth angle identifies the amount of rotation of the X and Y reference axes together about the Z axis to a new position in which the X axis is aligned with the center of the sensor in the Z direction. The new positions of the X and Y axes are defined as X' and Y' respectively.

The value $\omega_{els}$ is the elevation angle of the sensor. The elevation angle identifies the amount of rotation of the X' and Z axes together about the Y' axis to a new position in which the X' axis is aligned with the center of the sensor S. The new positions of the X' and Z axes are defined as X" and Z' respectively.

The value $\omega_{ros}$ is the roll angle of the sensor. The roll angle identifies the amount of rotation of the Y' and Z' axes together about the X" axis to a new position defining new axes Y" and Z" respectively. The sensor is oriented in the X", Y", Z" reference frame, and this orientation is defined by the values $\omega_{azs}$, $\omega_{els}$ and $\omega_{ros}$.

The combined power of all the sensor data is inversely proportional to the distance of the sensor from the source. The ratio between the sensor data components, created by the individual source coils, will determine the x, y, z position coordinate of the sensor. The ratio between the individual sensor coil data will determine the orientation of the sensor.

Because the medical instrument is free to move with respect to the transmitter at speeds that may be faster than the rate at which the electronics can process the information, the speed of the instrument should be monitored. If the speed of movement of the instrument is above a defined threshold, then inconsistent sensor readings should be ignored until the speed falls below the threshold. The speed may be monitored by calculating a weighted sum of the differences between each of the x, y, and z coordinates at successive time intervals $t_1$ and $t_2$.

The presence of a signal from another source, or the magnetic field of the eddy current in a conductive object, or the field distorting effect of a ferro-magnetic object will change the magnitude/direction of the original magnetic field of the source. This will result in an error in the sensor position/orientation.

In a preferred embodiment involving field integrity detection and with reference to FIGS. 1–3, a reference sensor 37 may be securely mounted on the transmitter assembly 12 at a fixed distance from the center of the transmitter 36. The location and orientation of this reference sensor should be determined through a calibration process under controlled conditions, and thereafter continuously calculated and verified. In certain embodiments a weighted sum of all six sensor output parameters $x_s$, $y_s$, $z_s$, $\omega_{azs}$, $\omega_{els}$, and $\omega_{ros}$ may be continuously monitored as an indication of compromised field integrity.

As also noted above and shown in FIGS. 7–12, the remote sensor 58 may include a plurality of sensors (62,64) the outputs of which are compared for error detection purposes. Potential error conditions that would be detectable by such a system include sensor failure where one sensor ceases to operate properly, as well as uneven localized field distortions in the area of the medical instrument.

It has further been found that simply comparing the sensor outputs may not sufficiently identify all types of error conditions that can occur, even if the distance between the sensors is taken into account. Such a potentially undetectable error condition may exist when a foreign ferromagnetic object enters the electromagnetic field and produces identical distortions at each of the sensors. This may be the case, for example if the foreign object has uniform ferromagnetic properties, if the foreign object approaches the two sensors from the same distance and at the same rate, and if the sensors are equidistant from the generator.

In this situation the outputs of the sensors would produce identical outputs and an error detection signal might therefore not be produced even though a foreign object would be in the electromagnetic field altering the electromagnetic field as well as the sensed position data. Although the use of additional sensors may reduce the risk of this occurring, it does not eliminate the possibility of an error condition being undetected.

Figure 25:
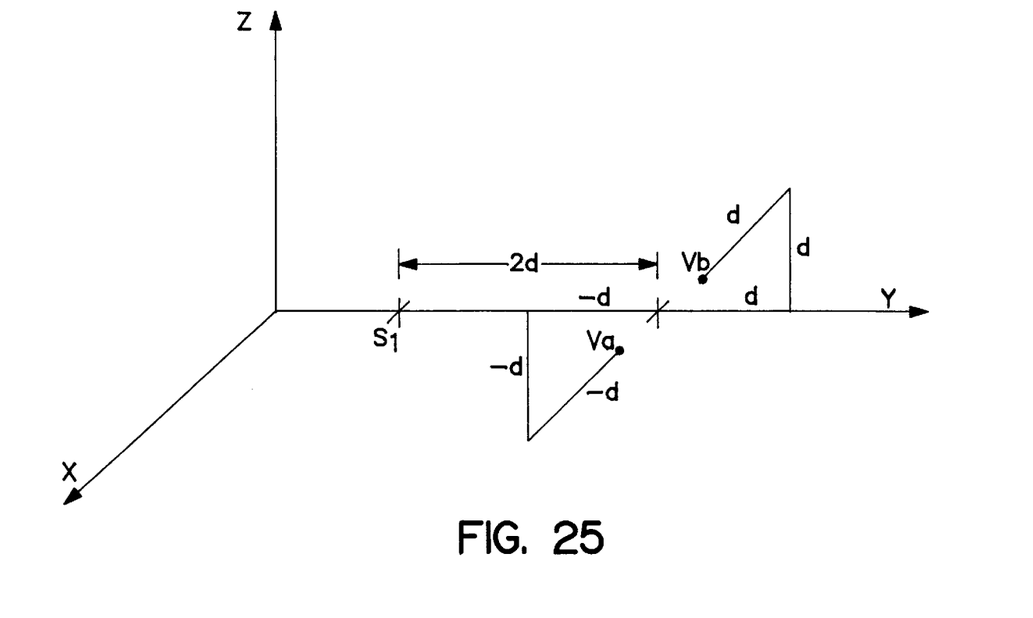

It has been discovered that an error detection system sufficient to identify localized uniform distortions in the area of the medical instrument or headset may be designed using two sensors separated by a fixed distance as shown in FIGS. 7–12 and by monitoring the locations of two or more virtual points. As shown in FIG. 25, the sensors $S_1$ and $S_2$ are separated from each other by a distance $2d$ and for convenience defined to be positioned along an axis such as the Y axis as shown. Sensor $S_1$ uniquely defines an X-Z plane in which it is located, and $S_2$ uniquely defines an X-Z plane in which it is located as shown. A first virtual location $v_a$ is chosen to be between the X-Z planes defined by the sensors, while a second virtual location $v_b$ is chosen to be outside of the X-Z planes defined by the sensors as shown in FIG. 11. The locations $v_a$ and $v_b$ are virtual locations that are continuously calculated and compared with factory defined positions.

Figure 24:
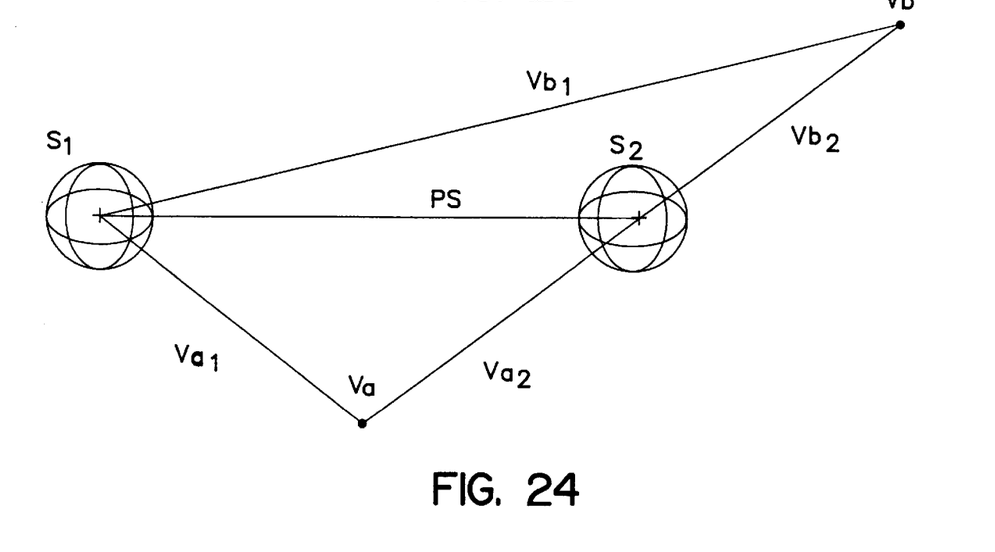
FIGS. 24 and 25 are diagrammatic views of the principles of an error detection calculation process in accordance with an embodiment of the invention.

In the embodiment diagrammatically shown in FIGS. 24 and 25 the virtual points $v_a$ (-d,-d,-d with respect to $S_2$) and $v_b$ (d,d,d with respect to $S_2$) are equidistant from $S_2$. The sensor $S_2$ is the protected sensor in this embodiment, and the sensor $S_1$ is used as a reference to provide the error detection for $S_2$. The magnitude of the resultant vector from $S_2$ to $v_a$ is the same as that from $S_2$ to $v_b$ but opposite in direction, and this magnitude is approximately one half of the distance between $S_1$ and $S_2$.

The locations of $v_a$ and $v_b$ in the reference coordinate system (i.e., with respect to $S_1$) must be calculated and will be referred to as $v_{a1}$ and $v_{b1}$. The location (PS) and the orientation of the protected sensor (S1) with respect to the reference sensor must be determined. The attitude matrix (A) is calculated from the orientation values of the protected sensor:

$$\begin{bmatrix} \cos\omega_{azs} \cdot \cos\omega_{els} & \sin\omega_{azs}\cos\omega_{els} & -\sin\omega_{els} \\ \cos\omega_{azs} \cdot \sin\omega_{els} \cdot \sin\omega_{ros} - \sin\omega_{azs} \cdot \cos\omega_{ros} & \cos\omega_{azs} \cdot \cos\omega_{ros} + \sin\omega_{azs} \cdot \sin\omega_{els} \cdot \sin\omega_{ros} & \cos\omega_{els} \cdot \sin\omega_{ros} \\ \cos\omega_{azs} \cdot \sin\omega_{els} \cdot \cos\omega_{ros} + \sin\omega_{azs} \cdot \sin\omega_{ros} & \sin\omega_{azs} \cdot \sin\omega_{els} \cdot \cos\omega_{ros} - \cos\omega_{els} \cdot \cos\omega_{ros} & \cos\omega_{els} \cdot \sin\omega_{ros} \end{bmatrix} \quad (5)$$

Then the locations of the virtual points are calculated as:

$$V_{a1} = A \cdot V_{a2} + PS$$

$$V_{b1} = A \cdot V_{b2} + PS$$

Figure 26:
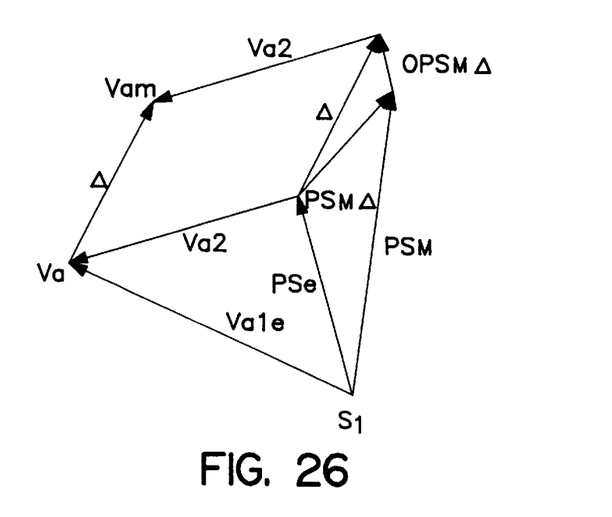
FIGS. 26 and 27 are diagrammatic views of the errors detected by the process of FIGS. 24 an 25.

To establish a reference value for the virtual point location in the reference sensor coordinate system, a measurement is taken in a distortion free environment during factory calibration. These stored reference values are called $v_{ae}$ and $v_{be}$. Throughout the use of the system, the actual measured values of the virtual points ($v_{am}$, $v_{bm}$) are compared to the stored reference values for the virtual points ($v_{ae}$, $v_{be}$). If the distance between the established and measured location (Δ) for either virtual point is larger than a preset value (ε), then a field integrity violation message is displayed and normal operation of the system is suspended. In particular and with reference to FIG. 26

$$|V_{alm} - V_{ale}| > \epsilon \text{ or } |v_{blm} - v_{ble}| > \epsilon$$

The operation is based in part on the principle that if the position error is being reduced by the orientation error at one virtual point, then the error will be increased at the other virtual point causing a field integrity violation signal to be generated. If for example, there is an error in the measured position and orientation of the protected sensor, then the measured value will have an error added to the established value. The field integrity checking is performed in this case as follows:

$$|((A_e + A_{m\Delta}) \cdot v_{a2} + PS_e + PS_{m\Delta}) - (A_e \cdot v_{a2} + PS_e)| > \epsilon$$

or $$|((A_e + A_{m\Delta}) \cdot v_{b2} + PS_e + PS_{m\Delta}) - (A_e \cdot v_{b2} + PS_e)| > \epsilon$$

which equals $$|A_{m\Delta} \cdot v_{a2} + PS_{m\Delta}| > \epsilon$$

or $$|A_{m\Delta} \cdot v_{b2} + PS_{m\Delta}| > \epsilon$$

Figure 27:
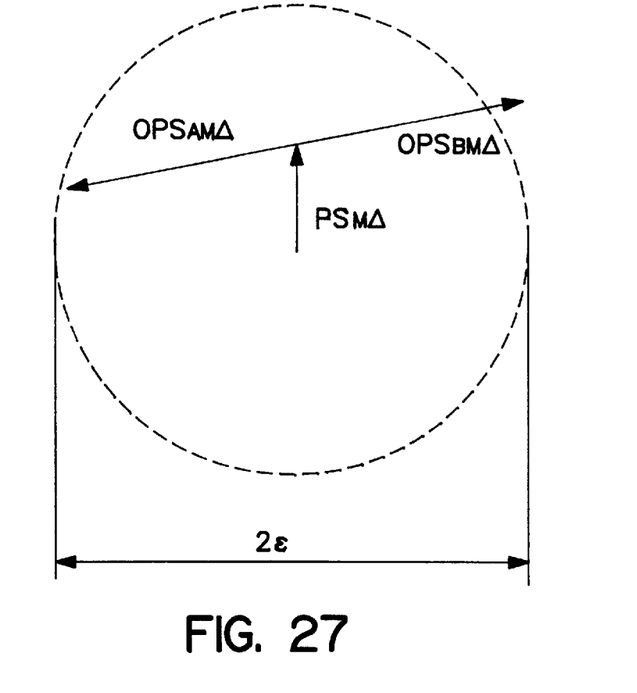

Substituting $$A_{m\Delta} \cdot v_{a2} = OPS_{am\Delta} \text{ and } A_{m\Delta} \cdot v_{b2} = OPS_{bm\Delta}$$

this relationship may be diagrammatically illustrated as shown in FIG. 27. The tip location of the medical instrument should be initially defined with respect to the protected sensor (S2), and used in determining the position of the tip with respect to the source.

The integrity of the field generated by the field generator may be monitored as discussed above by positioning a reference sensor a fixed distance from the generator, and continuously monitoring its position for any changes. The calculations involved in the above field integrity detection analysis regarding the two sensors $S_1$ and $S_2$, may be performed for a transmitter and single sensor field integrity detection system. Specifically, the calculations may be performed by substituting the field transmitter for the protected sensor ($S_2$), and by substituting the single sensor for the reference sensor ($S_1$). These field integrity analyses may also be used to identify the half field of the operation environment.

Figure 28:
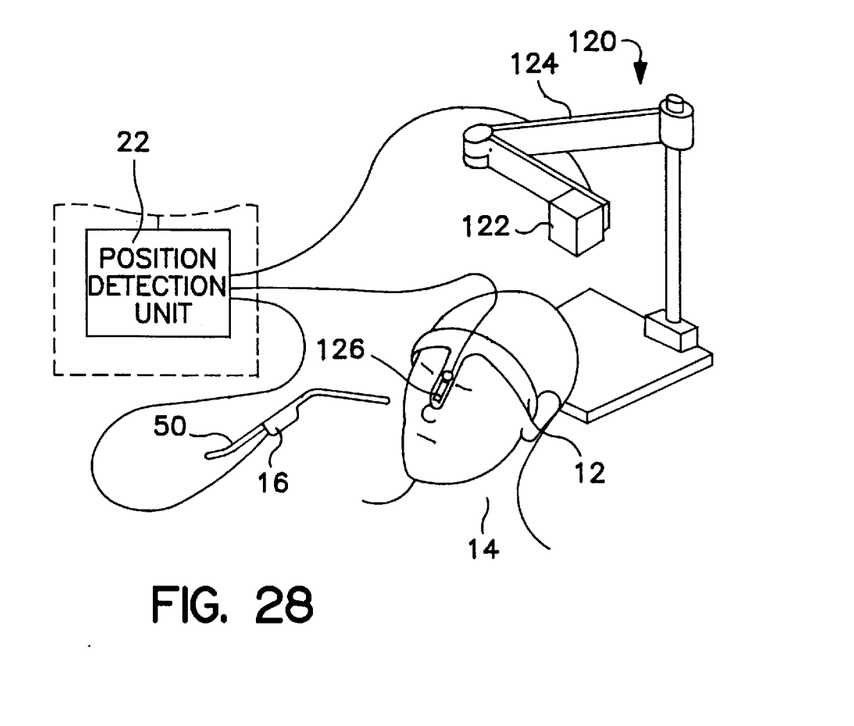
FIG. 28 is a diagrammatic view of another embodiment of the invention.

As shown in FIG. 28 in alternative embodiments of the invention a reference unit 120, including a field generator 122, may be positioned a small distance away from the portion of the patient's body (such as the head) 14 on an articulated arm 124. A headset 12 including a reference sensor 126 may be attached to the patient's body, and the medical instrument 16 may include a remote sensor 40 as discussed above with reference to FIGS. 1–6. Once the field generator 122 is positioned at a convenient location it may be fixed in place by securing the joints of the articulated arm. The position of the patient with respect to the field generator may accordingly be monitored. The position of the instrument 16 with respect to the patient may also be determined and the system may then operate to display the appropriate prerecorded images as discussed below.

In various embodiments, the position of the field generator 88 may be adjusted during the surgical operation by moving the articulated joints. If neither the remote sensor 40 nor the reference sensor 126 are moved with respect to one another, then moving the field generator 122 should not affect the position detection system. If the accuracy of the system depends at all on the relative positions of the field generators 122 and the sensors 40, 126, then it may be desirable to move the field generator 122 during the surgical operation. This may be the case, for example, if the system relies on the near-field characteristics of a multiplexed magnetic field wherein it might be desirable to keep the sensors 40, 126 generally equidistant from the generator 122. In still further embodiments, the system may periodically prompt the user to reposition the generator 122 such as through visual cues on the display. Those skilled in the art will appreciate that the relative positioning of the field generator and the one or more field sensors is in no way limited to those shown.

Figure 29:
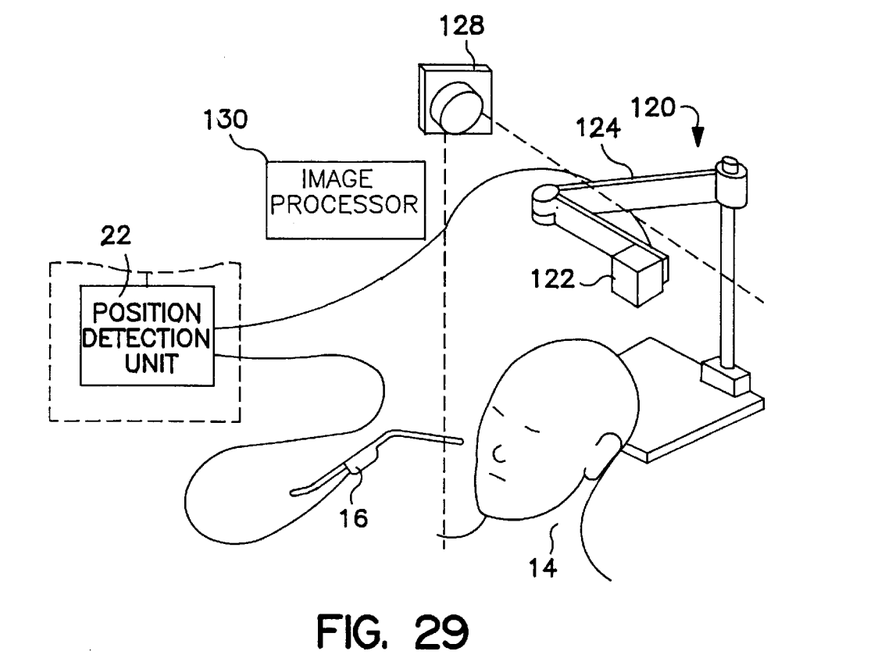
FIGS. 29–32 are diagrammatic views of further embodiments of systems of the invention.

The monitoring of the position of the patient may be accomplished by means other than using a headset and reference sensor. For example, a camera 128 connected to an image processor 130 may be positioned to record the location of the field generator with respect to the target operation site of the patient as shown in FIG. 29. If either the patient or the field generator is moved, the image processor 130 will identify the amount of relative change in location and advise the position detection unit 22 accordingly. Additional cameras positioned to view the patient from a variety of directions may be employed in further embodiments.

Figure 30:
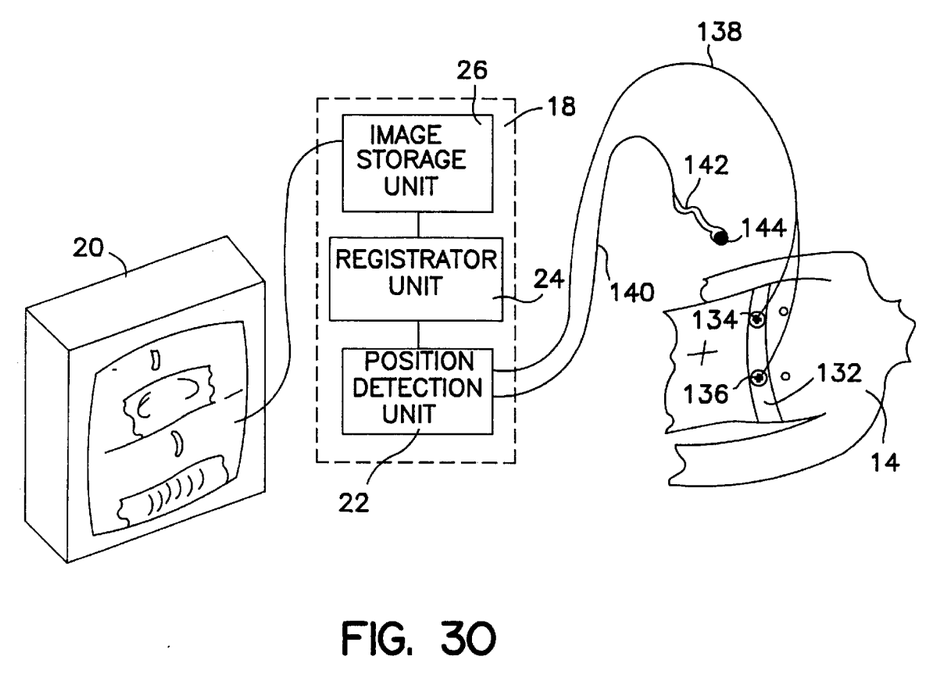

As shown in FIG. 30 in an alternate embodiment, the system may include a flexible band 132 for secure attachment to a portion of a patient's body 14 (e.g., a head or chest). The band 132 includes field generator 134 and a reference sensor 136 that provides feedback to the signal generator in the position detection unit 22. The position detection unit 22 is connected via communication lines 138 to the flexible band 132, and is connected via communication lines 140 to a flexible medical instrument 142 having a remote sensor at its tip 144. Because the medical instrument 142 is not rigid, the sensor should be positioned sufficiently close to the tip of the instrument 142 to provide accurate position detection and monitoring within the patient's body. The display 20 may indicate the relative orientation of the instrument 142 on one or more images as shown.

Figure 31:
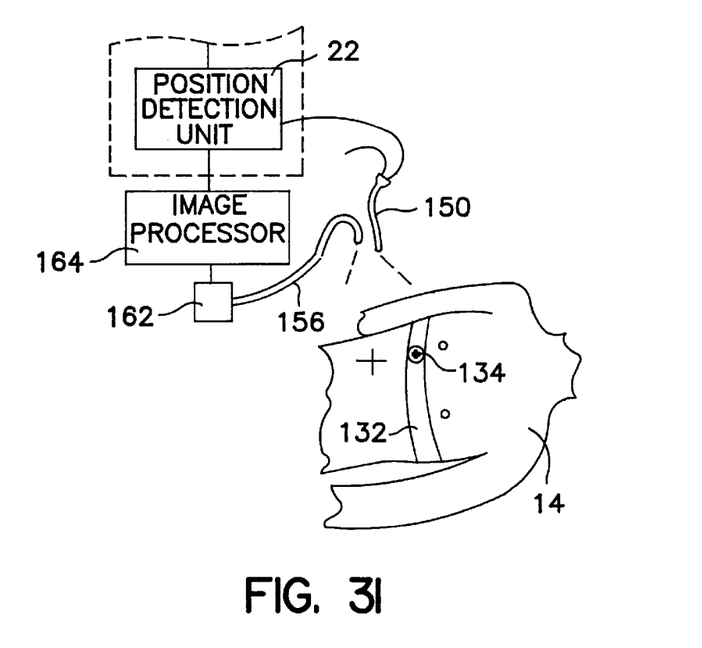
Figure 32:
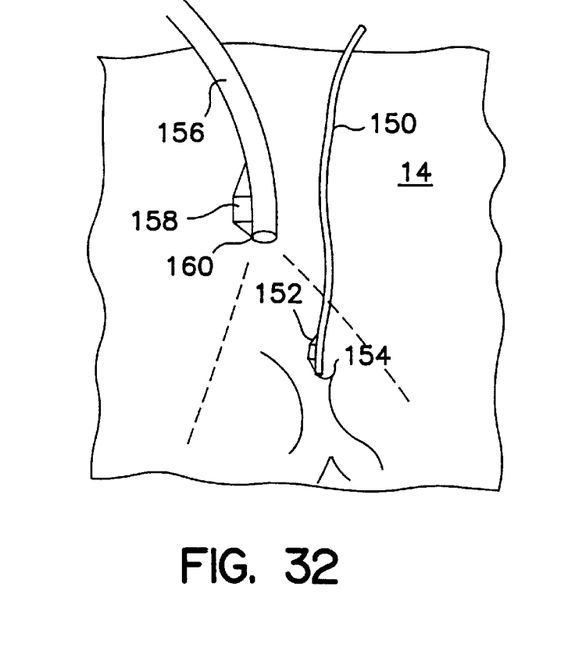

As shown in FIGS. 31 and 32 a system of the invention may include a flexible medical instrument 150 having a sensor 152 at its distal tip 154, and a fiber optic endoscope 156 having a sensor 158 at it distal tip 160. The fiber optic endoscope 156 is connected at its proximal end to a camera 162 which is in communication with an image processor 164. Because the field generator 134 on the reference band 132 may move, for example as the patient breaths, the location of the remote sensor 152 may appear to move when in fact the medical instrument 150 has not moved.

To correct for this problem, the fiber optic endoscope 156 can be used to monitor the position of the tip 154 of the instrument 150 with respect to the inside of the patient's body as shown. Any sensed movement of the sensor 152 with respect to the field generator 134 can be evaluated with reference to whether the tip 154 has moved with respect to the interior of the patient's body. If the camera observes that the tip 154 has not moved, but the sensor 152 indicates that it has moved, then the system can identify that such movement was due to the movement of the field generator and not the sensor 152. The system may then automatically correct for such variation. Further, the fiber optic endoscope 156 itself may include a sensor 158 for detecting whether the tip 160 of the fiber optic has moved. This should further enhance the accuracy of the correction system. Also, the camera 162 may provide continuous registration of the prerecorded images based on the internal structure of the patient's body.

It will be understood by those skilled in the art that numerous variations and modifications may be made to the above described embodiments without departing from the spirit and scope of the present invention.

We claim:

1. A medical instrument for use in a system for monitoring the position of a medical instrument with respect to a patient during surgery, said medical instrument comprising:

receiving means for releasably receiving a removable position detection unit for use in monitoring the position of said medical instrument with respect to a patient during surgery, and identification means for distinguishing said medical instrument from other medical instruments to which said position detection unit may be releasably attached.

2. A medical instrument as claimed in claim 1, wherein said identification means includes at least one magnetic element on said medical instrument and said position detection unit includes at least one magnetic field sensor, wherein at least some of said magnetic elements and magnetic field sensors mutually align when said position detection unit is received by said medical instrument.

3. A medical instrument as claimed in claim 1, wherein said position detection unit includes an electromagnetic signal receiver for receiving three alternating orthogonally disposed electromagnetic fields.

4. A medical instrument for use in a system for monitoring the position of a medical instrument with respect to a patient during surgery, said medical instrument comprising:

receiving means for releasably receiving a removable position detection unit for use in monitoring the position of said medical instrument with respect to a patient during surgery, said position detection unit including an electromagnetic signal receiver for receiving three alternating orthogonally disposed electromagnetic fields; and identification means for distinguishing said medical instrument from other medical instruments to which said position detection unit may be releasably attached, said identification means including at least one magnetic element on said medical instrument.

5. A medical instrument for use in a system for monitoring the position of a medical instrument with respect to a patient during surgery, said medical instrument comprising:

position detection means for monitoring the position of said medical instrument with respect to a patient during surgery, and releasable attachment means for releasably securing said position detection means to said medical instrument.

6. A medical instrument as claimed in claim 5, wherein said position detection means includes a sensor for sensing a three dimensional position characteristic field.

7. A medical instrument as claimed in claim 5, wherein said position detection means further permits the monitoring of the position of said medical instrument with respect to a patient during surgery irrespective of the position of said patent in an operating environment.

8. A medical instrument as claimed in claim 5, wherein said position detection means includes two sensors for sensing a three dimensional position characteristic field.

9. A medical instrument as claimed in claim 5, wherein said position detection means includes an electromagnetic field sensor.

10. A medical instrument as claimed in claim 5, wherein said medical instrument further includes an identification means for distinguishing said medical instrument from other medical instruments to which said position detection unit may be releasably attached.

* * * * *